United States Patent [19]

Inglis et al.

[11] Patent Number: 4,822,364
[45] Date of Patent: Apr. 18, 1989

[54] ELBOW JOINT PROSTHESIS

[75] Inventors: Allan E. Inglis, Rye, N.Y.; Chitranjan S. Ranawat, Alpine, N.J.; Albert H. Burstein, Stamford, Conn.

[73] Assignee: New York Society for the Relief of the Ruptured and Crippled, Maintaining the Hospital for Special Surgery, New York, N.Y.

[21] Appl. No.: 136,149

[22] Filed: Dec. 21, 1987

[51] Int. Cl.[4] ............................................... A61F 2/38
[52] U.S. Cl. ...................................................... 623/20
[58] Field of Search .................................... 623/18, 20

[56] References Cited

U.S. PATENT DOCUMENTS

| 3,918,101 | 11/1975 | Lagrange et al. | 623/20 |
| 3,990,117 | 11/1976 | Pritchard et al. | 623/20 |
| 3,996,624 | 12/1976 | Noiles | 623/20 |
| 4,112,522 | 9/1978 | Dadurian et al. | 623/18 |
| 4,131,956 | 1/1979 | Treace | 623/20 |
| 4,293,963 | 10/1981 | Gold et al. | 623/20 |
| 4,383,337 | 5/1983 | Volz et al. | 623/20 |
| 4,655,778 | 4/1987 | Koeneman | 623/18 X |

FOREIGN PATENT DOCUMENTS

| 2334265 | 1/1975 | Fed. Rep. of Germany | 623/20 |
| 0719623 | 3/1980 | U.S.S.R. | 623/20 |

OTHER PUBLICATIONS

Inglis et al., "Total Elbow Replacement", Dec. 1980, Journal of Bone and Joint Surgery, vol. 62-A, No. 8, pp. 1252-1258.
Ewald et al., "Capitellocondylar Total Elbow Arthroplasty", Dec. 1980, Journal of Bone and Joint Surgery, vol. 62-A, No. 8, pp. 1259-1263.
Allan E. Inglis, "Tri-Axial TM Total Elbow Prosthesis Surgical Technique", 1984, Johnson & Johnson Products, Inc. brochure.
Ralph W. Coonrad, "Coonrad II Total Elbow Surgical Technique", revised Jan. 1981.
Rowland W. Pritchard, "Pritchard ERS TM with Porocoat ® Surgical Procedure", 1983, DePuy brochure.
"Pritchard Total Elbow System", 1984, DePuy brochure.
"London Total Elbow", Dow Corning Wright brochure.

Primary Examiner—Richard J. Apley
Assistant Examiner—David J. Bender
Attorney, Agent, or Firm—Brumbaugh, Graves, Donohue & Raymond

[57] ABSTRACT

An elbow joint prosthesis having a metal humeral component, the head of which has flanges forming a recess in which a U-shaped plastic insert is nested. A boss projecting anteriorly from the head portion of a metal ulnar component is received within the insert with latero-medial clearance for laxity. A tubular plastic sleeve is received in axle holes in the ulnar boss and the legs of the plastic insert, and an axle spanning the flanges of the humeral component and extending through the sleeve bore connects the ulnar component to the humeral component for articulation. Clearance between the sleeve and the axle hole of the ulnar boss provides laxity up to nominal limits, beyond which elastic deformation of plastic at contact areas of the sleeve and insert restrains rotational and angular motions under supination, pronation and varus-valgus angulation of the arm, absorbing energy in the process. Lateral and medial protuberances on the proximal portion of the humeral head enhance support of the humeral component in strong bone of the distal humerus at the border of the olecranon depression.

7 Claims, 4 Drawing Sheets

ELBOW JOINT PROSTHESIS

BACKGROUND OF THE INVENTION

Within the past few years, it has become increasingly recognized by orthopaedic surgeons that implant arthroplasty of the elbow is often necessary to restore function to and eliminate pain from elbow joints with severe surface damage. A significant factor in the increased treatment of diseased elbow joints by implant arthroplasty is the availability of well-engineered elbow joint prostheses that minimize failures of the implant and loosening of the cement-bone bond. Early designs provided virtually total constraint, thereby causing large loads to be exerted on the prosthesis at the limits of the range of articular motion and in inhibiting angulation in the varus-valgus plane and laxity in supination and pronation. The high loading produced a high incidence of implant failures and loss of bone-cement retention.

Presently available elbow joint prostheses are designed to permit limited laxity during supination, pronation and varus-valgus angulation, thereby allowing the tendons and muscles associated with the joint to absorb some of the loads and correspondingly reduce the loads imposed on the prosthesis at the limits of motion. One very successful elbow prosthesis developed at the Hospital for Special Surgery (the assignee of the present invention) and produced under license as the "Tri-axial ™ Prosthesis" employs a unique "snap-fit" articulation in which a U-shaped plastic bushing attached by small pins to a metal humeral component accepts lateral and medial projections on a boss portion of an ulnar component within depressions in the legs of the bushing. The interaction of the bushing and the projections provides rotational and varus-valgus angular laxity in the prosthetic joint by permitting motions of the projections on the ulnar boss within the depressions of the humeral bushing, thereby absorbing energy and reducing loads imposed on the prosthesis.

While the "Tri-axial Prosthesis" has the very important advantages of virtually eliminating prosthesis failures and greatly reducing the possibility of loss of retention, a trade-off for these advantages is an increased likelihood of displacement of the joint—i.e., dislodgement of the ulnar boss from the humeral bushing.

SUMMARY OF THE INVENTION

An object of the present invention is to provide an elbow joint prosthesis that provides a good functional range of motion with appropriate laxities during supination, pronation and varus-valgus angulations throughout the range of motion, thereby permitting motions of the joint approximating those of the anatomical elbow joint. A further object is to eliminate the possibility of dislocation of the joint. Still another object is to improve compressive load transfers between the prosthesis components and between the humeral component and the humerus.

The foregoing and other objects are attained, according to the present invention, by an elbow joint prosthesis that comprises: a metal humeral component that includes a stem portion adapted to be received in the medullary canal of a distal humeral shaft and a head portion adapted to be received in a resected portion of a distal humerus intermediate the internal and external humeral condyles and including a lateral flange and a medial flange defining between them a recess opening distally, anteriorly and posteriorly; a metal ulnar component that includes a stem portion adapted to be received in the medullary canal of the proximal ulnar shaft, a head portion adapted to be received in a resected portion of the olecranon of an ulna and a boss portion extending generally anteriorly from the head portion and adapted to be received in the recess of the humeral component; and a plastic humeral insert component nested in the recess and including a base portion and a pair of leg portions selectively engageable between the boss of the ulnar component and the head portion of the humeral component throughout the range of motion of the prosthesis. As described generally thus far, the prosthesis of the present invention is similar to the known "Tri-axial Prosthesis" described above.

The present invention is characterized in that the flanges of the humeral component, the legs of the insert component and the boss portion of the ulnar component have axle holes aligned along a lateromedial axis, in that a metal axle extends through the holes and connects the humeral and ulnar components for articulation, in that a plastic sleeve is interposed between the portions of the axle within the holes of the insert component legs and the ulnar component boss, and in that the boss of the ulnar component is in lateral clearance from the walls of the insert component legs and the sleeve is in radial clearance with the axle hole in the ulnar component boss so as to provide laxity under pronation, supination and varus-valgus angulation of the arm.

The prosthesis of the present invention may include the following preferred characteristics alone or in various combinations.

(1) The boss of the ulnar component has a convex spherical articular surface along its superior, anterior and inferior aspects, and the base portion of the insert component bears against an inferior surface of the head portion of the humeral component and has a concave spherical inferior articular surface complementary to and engageable by the ulnar spherical articular surface throughout the range of motion of the prosthesis for transfer of compressive loads.

(2) Each leg portion of the insert component has an outwardly extending peripheral U-shaped rib engaging the anterior, posterior and distal aspects of a corresponding flange portion of the humeral component, and the head portion of the ulnar component has generally anteriorly facing concave bearing surfaces, one laterally of and one medially of the boss portion, adapted to engage selectively the respective ribs of the insert component upon selected extents of varus-valgus angulation and pronation-supination rotation of the arm but in clearance with the ribs in the absence of such angulations and rotations.

(3) The distal portions of the ribs have convex circular cylindrical surfaces having their centers coincident with the axis of the axle, and the bearing surfaces of the head portion of the ulnar component are concave circular cylindrical surfaces that are complementary to and slightly oblique to the cylindrical surfaces of the ribs.

(4) The axle hole in the boss portion of the ulnar component has a cylindrical central portion and an outwardly tapered lateral portion on each side of the central portion, and the sleeve is in clearance fit with the axle hole of the boss portion so that selected amounts of varus-valgus angulation and pronation-supination rotation of the prothestic joint are afforded without compression binding of the sleeve between the axle hole of the boss portion and the axle.

(5) The surfaces of the leg portions of the insert component defining the recess have inferiorly divergent segments adjacent their distal extremities, and the boss portion of the ulnar component has lateral and medial surfaces that are normally in clearance with said surfaces of the insert component leg portions so as to allow selected amounts of varus-valgus angulation and pronation-supination rotation of the prosthetic joint without compression binding but are engageable with the divergent segments to restrain such angulation and rotation and absorb energy.

(6) The head portion of the humeral component has bulbous protuberances on its lateral and medial aspects for enhanced transfer of compression loads from the humeral component to the bone of the inferior distal humerus.

(7) The bulbous protuberances are shaped to match generally the borders of the olecranon depression.

The laxity of the prosthesis of the present invention allows rotation and angulation between the upper arm and forearm to extents comparable to those accommodated by the anatomical elbow joint. Such motions are restrained by the soft tissues of the arm, thereby reducing loads on the prosthesis at the nominal limits of motion designed into the prosthesis. Beyond the nominal limits some additional rotation and angulation are permitted by elastic deformation of the plastic insert and sleeve, which absorb the energy of contacts at the limits of free motion and cushion what otherwise might be a sharp impact or shock load that could cause the bone-cement-metal fixation structures to loosen. All transfers of forces between the components are from metal to plastic to metal which not only provides shock absorption but reduces friction.

For a better understanding of the invention, reference may be made to the following description of an exemplary embodiment, taken in conjunction with the figures of the accompanying drawings.

DESCRIPTION OF THE DRAWINGS

FIG. 1—elevational of the lateral aspect;
FIG. 2—elevational of the posterior aspect;
FIG. 3—plan of the inferior aspect;
FIG. 4—detail partial cross-sectional along 4—4 of FIG. 1 and on an enlarged scale;
FIGS. 5 to 7—cross-sectionals indicated in FIG. 1.
FIG. 8—elevational of the medial aspect;
FIG. 9—elevational of anterior aspect;
FIG. 10—cross sectional along 10—10 of FIG. 8 on enlarged scale;
FIGS. 11 and 12—cross-sectionals indicated in FIG. 8;
FIG. 13—enlarged detail indicated by circle 13 in FIG. 8.

DESCRIPTION OF THE EMBODIMENT

Figure 1:
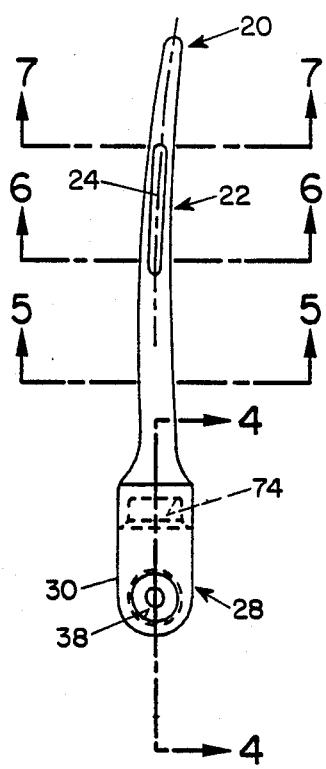
FIGS. 1 to 7 are views of the humeral component for the right elbow, as follows.
Figure 2:
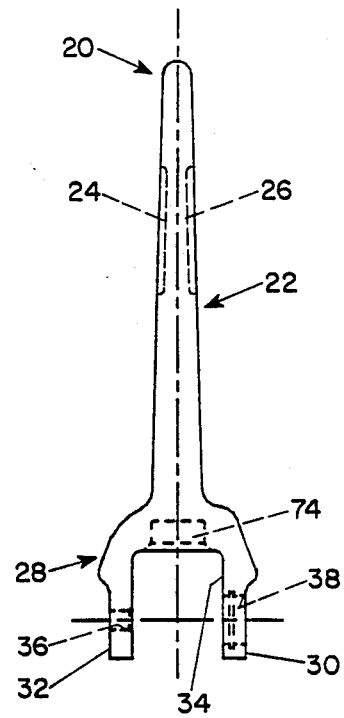
Figure 3:
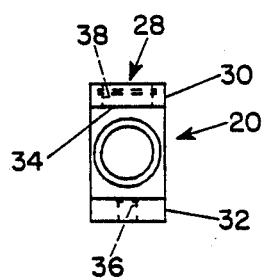
Figure 4:
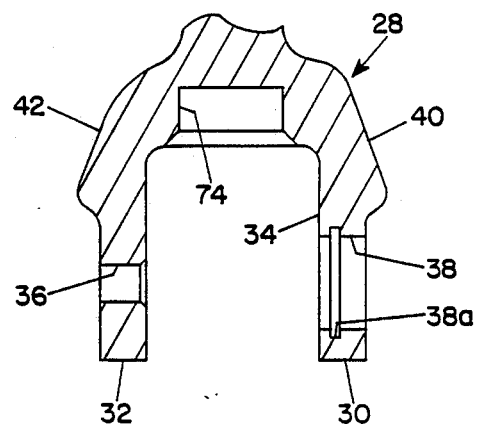
Figure 5:
Figure 6:
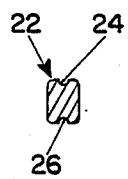
Figure 7:
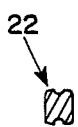
Figure 8:
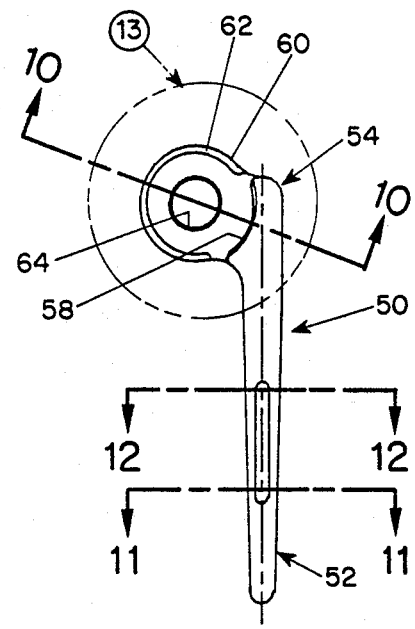
FIGS. 8 to 13 are views of the ulnar component, as follows.
Figure 9:
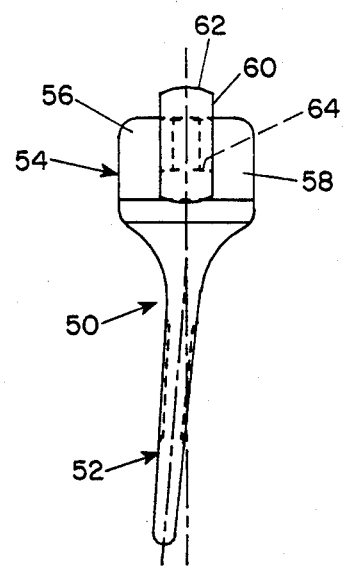

The humeral component 20 (FIGS. 1 to 7) is made from a surgical grade metal, such as Ti-6Al-4V. It has a stem portion 22, which is curved to fit to the anatomical curvature of the medullary canal of the distal humeral shaft. Cement grooves 24 and 26 on its lateral and medial aspects provide enhanced retention in the polymethyl methacrylate (PMMA) cement used to secure the component to the humerus. The stem is of rectangular cross-section and tapered (FIGS. 5 to 7) and joins at a smoothly curved juncture a generally U-shaped head portion 28, the distally dependent lateral and medial flanges 30 and 32 of which define a recess 34 that opens inferiorly, anteriorly and posteriorly and have holes 36 and 38 for an axle (described below). Bulbous protuberances 40 and 42 on the proximal portions of the lateral and medial aspects of the humeral head portion 28 are shaped to match generally the lateral and medial borders of the olecranon depression of the humerus.

The distal humerus is resected by excision of the trochlea and by shaping of the excised region to expose the strong cancellous bone at the inner borders of the epicondyle and epitrochlea to match the bulbous protuberances. Hence, the implanted humeral component is well-supported laterally, medially and proximally by the bone of the vestigial distal humerus. Accordingly, compression loads on the prosthetic joint are transferred from the humeral component to the humerus mainly along the superior aspects of the head portion 28, thereby reducing the possibility of loosening of the prosthesis by loss of the cement-bone bond within the medullary canal or by bone resorption. Note that the lateral and medial protuberances 40 and 42 are intentionally shaped differently for optimal fitting to strong bone at the implant site. In the antero-posterior direction the head portion 28 is narrow to maximize the articular range of motion in extension and flexion.

Figure 10:
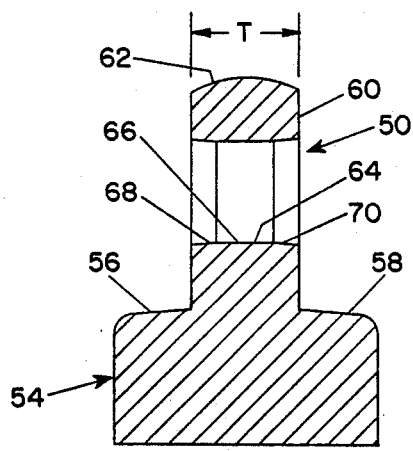
Figure 13:
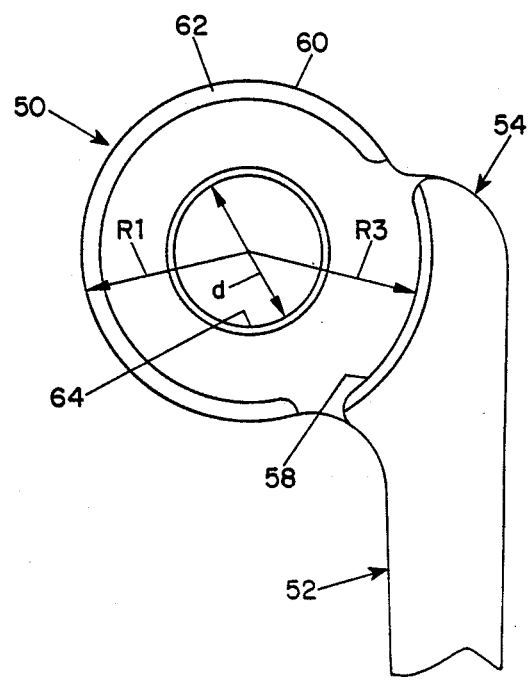
Figure 11:
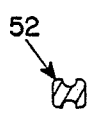
Figure 12:

The ulnar component 50 (FIGS. 8 to 13) is also of metal, such as Ti-6Al-4V. A tapered stem portion 52 of rectangular cross section and with cement grooves for enhanced fixation is oriented obliquely to a head portion 54, thus establishing an anatomically correct varus angle between the upper arm and forearm. The juncture between the stem and head is smoothly curved and presents superiorly and posteriorly a thick and broad plate-like body, the anterior aspect of which consists of two segments of concave cylindrical surfaces. The axes of the surfaces 56 and 58 are slightly oblique to that face generally anteriorly each other (see FIG. 10). Projecting anteriorly and slightly superiorly from the center of the head portion 54 is a boss 60 having parallel flat sides and a spherical surface 62 presented as a band inferiorly, superiorly, and anteriorly. The center of the spherical surface 62 coincides with the axis of a transverse axle hole 64, the center portion 66 of which is circular cylindrical and the end portions 68 and 70 of which are frusto-conical (tapered divergently outwardly). The ulnar component is implanted in the proximal ulna, which is prepared by resecting a notch for the head portion 54 in the anterior olecranon process and by opening and widening the floor of the notch for acceptance of the stem into the canal of the proximal ulnar shaft.

Figure 18:
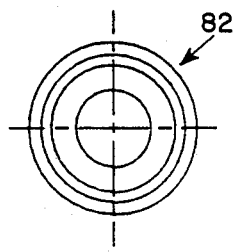
FIGS. 17 and 18 are half cross-sectional and end elevational views, respectively, of the axle sleeve.
Figure 17:
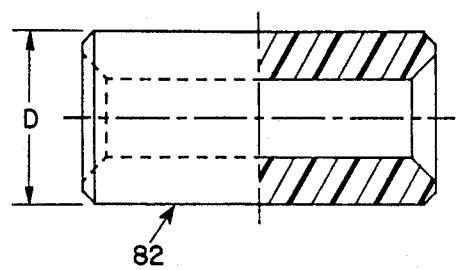
Figure 15:
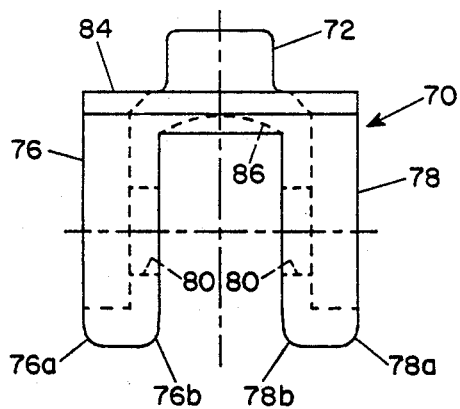
FIGS. 14 to 16 are inferior plan, anterior elevational and lateral elevational views, respectively, of the humeral insert component.
Figure 16:
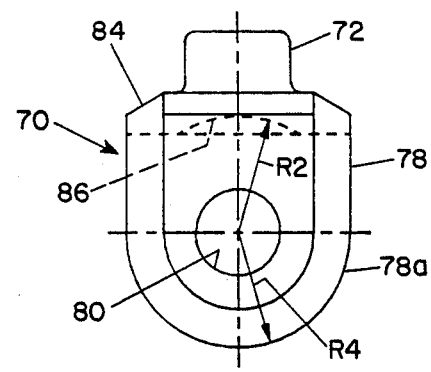
Figure 14:
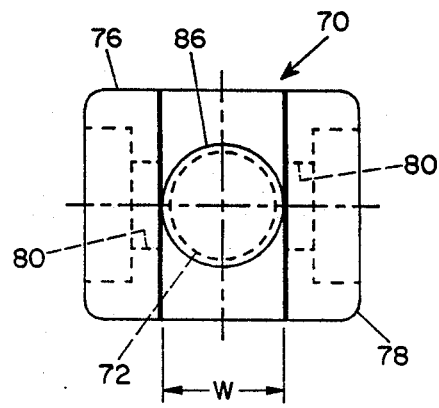

The insert component 70 (FIGS. 14 to 16) is made of ultra high molecular weight polyethylene (UHMWPE) and is symmetrical about its antero-posterior and latero-medial centerlines, which means it can be used in both elbows. It is generally U-shaped and has a round pin 72 that fits into a socket 74 (FIG. 4) in the base portion 28 of the humeral component 20. The outward aspect of each leg 76 and 78 has a recess shaped to match the profile of, and thus to receive, a flange 30, 32 of the humeral component and to define a bounding rib 76a, 78a that overlies the inferior, anterior and posterior margins of the respective flanges 30 and 32. (It is evident that FIGS. 14 to 16 are drawn to a larger scale than are FIGS. 1 to 3 but on the same scale as that of FIG. 4.) Each leg 76 and 78 has an axle hole 80. The distal extremity of each leg 76, 78 is a semi-cylindrical surface having its axis coincident with the axis of the axle holes 80. A tubular circular cylindrical sleeve 82 of UHMWPE (FIGS. 17 and 18, which are on a still larger scale than are FIGS. 14 to 16) is received with a close fit within the axle holes 80 of the legs 76 and 78 of the insert component 70. On the inferior surface of the base portion 84 of the insert component is a spherical depression 86, the center of which is at the intersection of the axis of the axle holes 80 with the latero-medial bisecting plane of the insert component 70.

Figure 19:
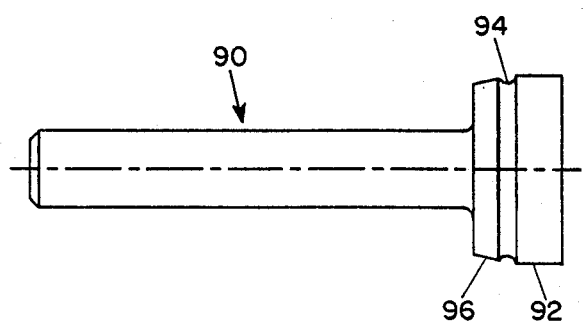
FIG. 19 is an elevational view of the axle.
Figure 20:
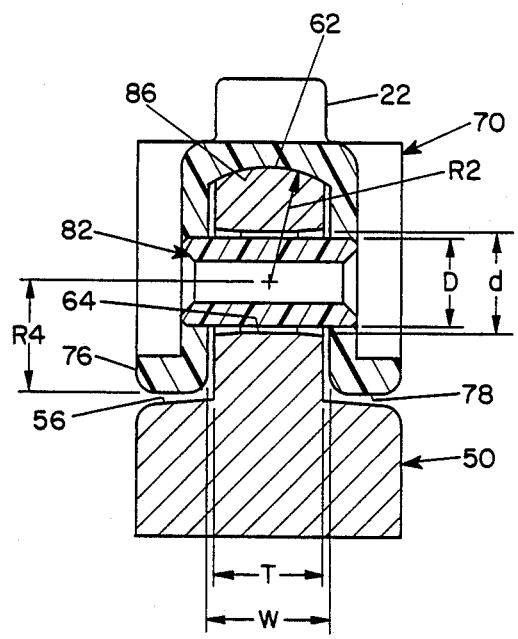
FIG. 20 is a partial assembly showing the insert connected to the ulnar component with the axle sleeve.

The axle 90 (FIG. 19) is of metal, such as Ti- 6Al-4V, joins all of the components of the assembled prosthesis and, of course, is installed after the humeral and ulnar components have been implanted and the insert component and sleeve have been nested in place in the receiving recess of the humeral component. The axle is received with a close fit through the bore of the sleeve 82, and its medial end extends with a close fit into the small axle hole 36 in the flange 32 of the humeral component. The head 92 of the axle has a groove 94 that accepts a resilient C-ring (not shown) that is pre-installed in a groove 38a (FIG. 4) in the large axle hole 38 in the flange 30. A tapered surface 96 on the inward border of the axle head expands the C-ring as the axle is pressed home, and the C-ring resiles into the groove 94 to lock the axle in place.

Several dimensional relationships and configurations of the components provide about 10 degrees of laxity (without restraint by the prosthesis) during pronation, supination and varus-valgus angulation, as follows:

(1) The latero-medial thickness T (FIG. 10) of the ulnar boss 60 is less than the width W (FIG. 14) of the receiving recess between the legs 76 and 78 of the insert component;

(2) The outside diameter D (FIG. 17) of the sleeve 82 is slightly less than the diameter d (FIG. 13) of the cylindrical center part 66 of the axle hole 64 in the ulnar boss 60 so the axle can nutate within the axle hole 64 to the extent allowed by the tapered end portions of the hole;

(3) The radius R1 of the spherical surface segment 62 at the margin of the ulnar boss 60 (FIG. 13) is equal t the radius R2 of the spherical depression 86 (FIG. 16) of the insert component 70;

(4) The radii R3 (FIG. 13) of the cylindrical surfaces 56 and 58 of the head portion of the ulnar component are greater than the radii R4 (FIG. 16) of the cylindrical surfaces at the distal extremities of the flanges 76 and 78 of the legs of the insert component 70. As mentioned above, the radii R3 and R4 have the same center. Therefore, the ulnar component can nutate within the receiving recess of the insert component;

(5) The inner distal extremities of the legs 76 and 78 of the insert component are bevelled at a small angle to provide contact areas 76b, 78b between the sides of the ulnar boss and the legs of the insert component 70.

The muscles and tendons of the arms keep the elbow joint tight, which maintains compression contact between the spherical border 62 of the ulnar boss 60 and the depression 86 of the insert component. In a neutral position of the ulnar boss within the receiving recess in the insert component, there is lateral clearance between the ulnar boss and the legs of the insert and radial clearance between the sleeve 82 and the axle hole 64 of the ulnar boss 60. Compression loads are transmitted from the ulnar boss to the spherical depression 86 in the base portion 84 of the insert component. The ulnar surfaces 56, 58 are in clearance with the edges of the insert flanges 76, 78.

The prosthesis provides laxity under supination, pronation and varus-valgus angulation by permitting latero-medial cocking and relative axial rotation of the ulnar component relative to the humeral assembly, which consists of the humeral component, insert component, sleeve and axle, due to the above-mentioned clearances. From extension through part of the full range of flexion, compression loads are transmitted at the superior extremity of the ulnar boss to the depression 86 of the insert. Cocking and rotational motions of the prosthetic joint occur freely—subject to soft tissue restraint but no restraint by the prosthesis—until restrained by contacts between the sleeve 82 and the axle hole 64 of the ulnar boss, between one of the surfaces 56, 58 of the ulnar head and the extremity of the corresponding flange 76, 78 of the insert, and between one of the side faces of the ulnar boss and the corresponding contact surfaces 76b, 78b.

All engagements between relatively moving surfaces for all motions (articular, rotational and angular) involve metal to plastic contact, which has two benefits—low friction for freedom of motion and energy absorption of impact loads at the limits of motion. The latter benefit reduces the possibility of loosening. All plastic surfaces subject to loading are backed-up by metal, which isolates stressed areas of plastic from bone and cement and prevents concentrated loads. As mentioned above, the carefully shaped protuberances on the head of the humeral component provide enhanced support for the humeral component by strong bone of the humerus, which provides greater assurance against bone resportion at the implant site.

We claim:

1. An elbow joint prosthesis comprising a metal humeral component that includes a stem portion adapted to be received in the medullary canal of a distal humeral shaft and a head portion adapted to be received in a resected portion of a distal humerus intermediate the internal and external humeral condyles and including a lateral flange and a medial flange defining between them a recess opening distally, anteriorly and posteriorly; a metal ulnar component that includes a stem portion adapted to be received in the medullary canal of the proximal ulnar shaft, a head portion adapted to be received in a resected portion of the olecranon of an ulna and a boss portion extending generally anteriorly from the head portion and adapted to be received in the recess of the humeral component; a plastic humeral insert component nested in the recess and including a base portion and a pair of leg portions selectively engageable between the boss of the ulnar component and the head portion of the humeral component throughout the range of motion of the prosthesis, the flanges of the humeral component, the legs of the insert component and the boss portion of the ulnar component having aligned axle holes extending latero-medially, a metal axle extending through the holes and connecting the humeral and ulnar components for articulation, a plastic sleeve interposed between the portions of the axle within the holes of the insert component legs and the ulnar component boss, the boss of the ulnar component being in lateral clearance from the walls of the insert component legs and the sleeve being in clearance with the hole in the ulnar component boss so as to provide laxity under pronation, supination and varus-valgus angulation of the arm the boss of the ulnar component having a convex spherical articular surface along its superior, anterior and inferior aspects, and the base portion of the insert component bearing against an inferior surface of the head portion of the humeral component and having a concave spherical inferior articular surface throughout the range of motion of the prosthesis for transfer of compressive loads.

2. An elbow joint prosthesis according to claim 1 wherein each leg portion of the insert component has an outwardly extending peripheral U-shaped rib engaging the anterior, posterior and distal aspects of a corresponding flange portion of the humeral component, and wherein the head portion of the ulnar component has generally anteriorly facing concave bearing surfaces, one laterally of and one medially of the boss portion, adapted to engage selectively the respective ribs of the insert component upon selected varus-valgus angulations and pronation-supination rotations of the arm but in clearance with the ribs in the absence of such angulations and rotations.

3. An elbow joint prosthesis according to claim 2 wherein the distal portions of the ribs have convex circular cylindrical surfaces having their centers coincident with the axis of the axle and wherein the bearing surfaces of the head portion of the ulnar component are concave circular cylindrical surfaces that are complementary to and slightly oblique to the cylindrical surfaces of the ribs.

4. An elbow joint prosthesis according to claim 3 wherein the axle hole in the boss portion of the ulnar component has a cylindrical central portion and an outwardly tapered lateral portion on each side of the central portion and wherein the sleeve is in clearance fit with the axle hole of the boss portion so that selected amounts of varus-valgus angulation and pronation-supination rotation of the prosthetic joint are afforded without compression binding of the sleeve between the axle hole of the boss portion and the axle.

5. An elbow joint prosthesis according to claim 1 wherein the inwardly facing surfaces of the leg portions of the insert component have inferiorly divergent segments adjacent their distal extremities, and wherein the boss portion of the ulnar component has lateral and medial surfaces that are normally in clearance with said surfaces of the insert component leg portions so as to allow selected amounts of varus-valgus angulation and pronation-supination rotations of the prosthetic joint without compression binding but are engageable with the divergent segments to restrain such angulations and rotations and absorb energy.

6. An elbow joint prosthesis according to claim 1 wherein the head portion of the humeral component has bulbous protuberances on its lateral and medial aspects for enhanced transfer of compression loads from the humeral component to the bone of the inferior distal humerus.

7. An elbow joint prosthesis according to claim 6 wherein the bulbous protuberances are shaped to match generally the borders of the olecranon depression.

* * * * *

UNITED STATES PATENT AND TRADEMARK OFFICE
CERTIFICATE OF CORRECTION

PATENT NO. : 4,822,364

DATED : April 18, 1989

INVENTOR(S) : Allan E. Inglis et al.

It is certified that error appears in the above-identified patent and that said Letters Patent is hereby corrected as shown below:

Col. 4, line 48, after "surfaces" insert --that face generally anteriorly--;
Col. 4, lines 49-50, delete "that face generally anteriorly";
Col. 5, line 54, "t the" should be --to the--;
Col. 7, line 17, after "surface" insert --complementary to and engageable by the ulnar spherical articular surface--.

Signed and Sealed this

Fifth Day of December, 1989

Attest:

JEFFREY M. SAMUELS

Attesting Officer     Acting Commissioner of Patents and Trademarks